US00PP12297P2

(12) United States Plant Patent
Houbraken

(10) Patent No.: US PP12,297 P2
(45) Date of Patent: Dec. 18, 2001

(54) SANVITALIA NAMED 'SANTIS 999-3'

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 09/448,071

(22) Filed: Nov. 23, 1999

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—Larry W. Stults; Bruce Vrana

(57) ABSTRACT

A new 'Sanvitalia' plant particularly distinguished by its proliferous character, dark leaves, stems with anthocyanin, good floridity with bright yellow flowers and green center. Flowering time is almost year round, depending on the growing conditions (especially temperature).

1 Drawing Sheet

BACKGROUND OF THE NEW PLANT

The present invention comprises a new distinct cultivar of Sanvitalia, botanically known as *Sanvitalia×hybrida,* native to Mexico. The new Sanvitalia plant was discovered in a controlled environment in Enkhuizen, the Netherlands, as a naturally occurring mutation of the *Sanvitalia×hybrida* 'Aztekengold' (unpatented). The new Sanvitalia plant was observed as a single plant in a large population of plants of the parent cultivar. The instant plant was grown under natural Dutch spring greenhouse conditions. Temperature day/night was 16/14° C., light level is very much depending on the weather. No growth regulators were applied. This new Sanvitalia plant will hereafter be referred to as 'Santis 99-3'. The new cultivar is being marketed under the name 'Cuzco'. This new plant is an annual.

DESCRIPTION OF THE DRAWING

This new Sanvitalia plant is illustrated by the accompanying photographic drawing which shows blooms, buds and foliage of the plant in full color, the color shown being as true as can be reasonably obtained by conventional photographic procedures. The photographic drawing was taken when the new plant was about 4 months old. After growing 3 months in the greenhouse, the plants were transplanted into the open field and grown under Dutch summer conditions. The photographs were taken in 1999.

DESCRIPTION OF THE NEW CULTIVAR

The following detailed descriptions set forth the distinctive characteristics of the new plant. The data which defines these characteristics were collected from asexual reproductions carried out in Enkhuizen, Netherlands. The plant history was taken on 12 weeks old plants, blossomed under additional light in a greenhouse under Elite regimes. Color references are primarily to the R.H.S. Colour Chart of The Royal Horticultural Society of London.

Plant Description

Classification — Botanical: *Sanvitalia×hybrida.*
Parentage selection from: 'Aztekengold'.
Growth habit: Spreading and half hanging.
Plant height: 20–30 cm.

Spreading area of plant: 40–50 cm.
Growth rate: Vigorous.
Strength: Good.
Branching character: Good branching.
Blooming period: Year round flowering, depending on temperature.
Branching: About 10–15 branches, depending on the number of times pinched, which stimulates branching. The number of blooms per branch is about 10, with a total per plant in full flower stage of about 100–150. This data is collected from a 3-month old plant. The plant was pinched 2 times. The flowers last about 25–30 days.

Stem Description

Diameter: 1–3 mm.
Shape: Cylindrical.
Anthocyanin pigmentation in the stem: 187A.
Anthocyanin pigmentation in the leaves (young and old): 147A.
Length of internode: 20–80 mm depending on the light where the plant is propagated.
Pubescence: Present.

Foliage Description

Phyllotaxis: Opposite.
Shape of leaf: Elliptic, with an obtuse base and acute apices. The leaf margin is entire. The color of the leaf vanation is 144A, and the shape is reticulate.
Texture: Hairy.
Length: 10–50 mm.
Width: 5–18 mm.
Depth of incision: No incision.
Color:
*Upper side.*—Dark green 147A.
*Lower side.*—Light green 147C.
Length of leaf stem: No leaf stem.

Flower Bud Description

Pedicel length: 15–25 mm.
Size:
*Diameter.*—3–7 mm.
*Length.*—3–4 mm.

Shape: Ball shape.

Flower Description

Direction: Ascending.
Shape of florets: Ray florets long, flat and narrow disc florets tubular.
Diameter total flower head: 10–20 mm.
Borne: Solitary.
Form: Capitulum with 1 series of ray florets and more series of disc florets.
Flower color:
*Ray flower.*—9A.
*Disc flower.*—6A (old) to 143A (young).
Overlapping of ray florets: Separate.
No. of ray florets: 13.
Receptacle shape: Convex, hemispherical.
Receptacle height: 4–5 mm.
Involucre: Bell shaped, bracts in one series.
Bracts:
*Size.*—4–5 mm.
*Color.*—137A.
*Number.*—5.
Size of the ray floret:
*Length.*—4–7 mm.
*Width.*—2–3 mm.
Calyx: Not visible.
Fragrance: Absent.
Reproductive organs: Ray florets female. Disc florets male.
Pedicel color: 165A.
Bud color: 143A.

Root Description

Root initiation: About 14 days at a soil temperature of about 21–22° C.
Time to develop roots: Cuttings taken from October until February will need 28 days to develop, whereas cuttings taken from February until October will need about 21 days to develop. The air temperature should be about 16–18° C. during the root phase.
Rooting habit: The rooting habit is fine and freely branching.
Achenes: Length×width=1.5 mm×1 mm. Color=200A–200C.

In the following Chart I, the colors of 'Aztekengold', which is the parent, and 'Santis 99-3' are compared on the main characteristics in which they differ from each other.

CHART I

| | 'Aztekengold' | 'Santis 99-3' |
|---|---|---|
| Upper leaf color | 137B | 147A |
| Lower leaf color | 147C | 147C |
| Stem color | 146C | 187A |
| Flower color | 14B | 9A |

In the following Chart II, the colors of 'Sunbini', which is another variety of the same market class, and 'Santis 99-3' are compared on the main characteristics in which they differ from each other.

CHART II

| | 'Sunbini' | 'Santis 99-3' |
|---|---|---|
| Upper leaf color | 137B | 147A |
| Lower leaf color | 148B | 147C |
| Stem color | 146C | 187A |
| Flower color | 13A | 9A |

Physiological and Ecological Characteristics

Good tolerance to heat and cold. Strong resistance to pests and diseases.

We claim:

1. A new and distinct variety of Sanvitalia plant, substantially as herein illustrated and described, characterized particularly as to novelty by its dark green leaves, stems with anthocyanin, and bright yellow flowers with green center and year-round flowering period, depending on the temperature.

* * * * *

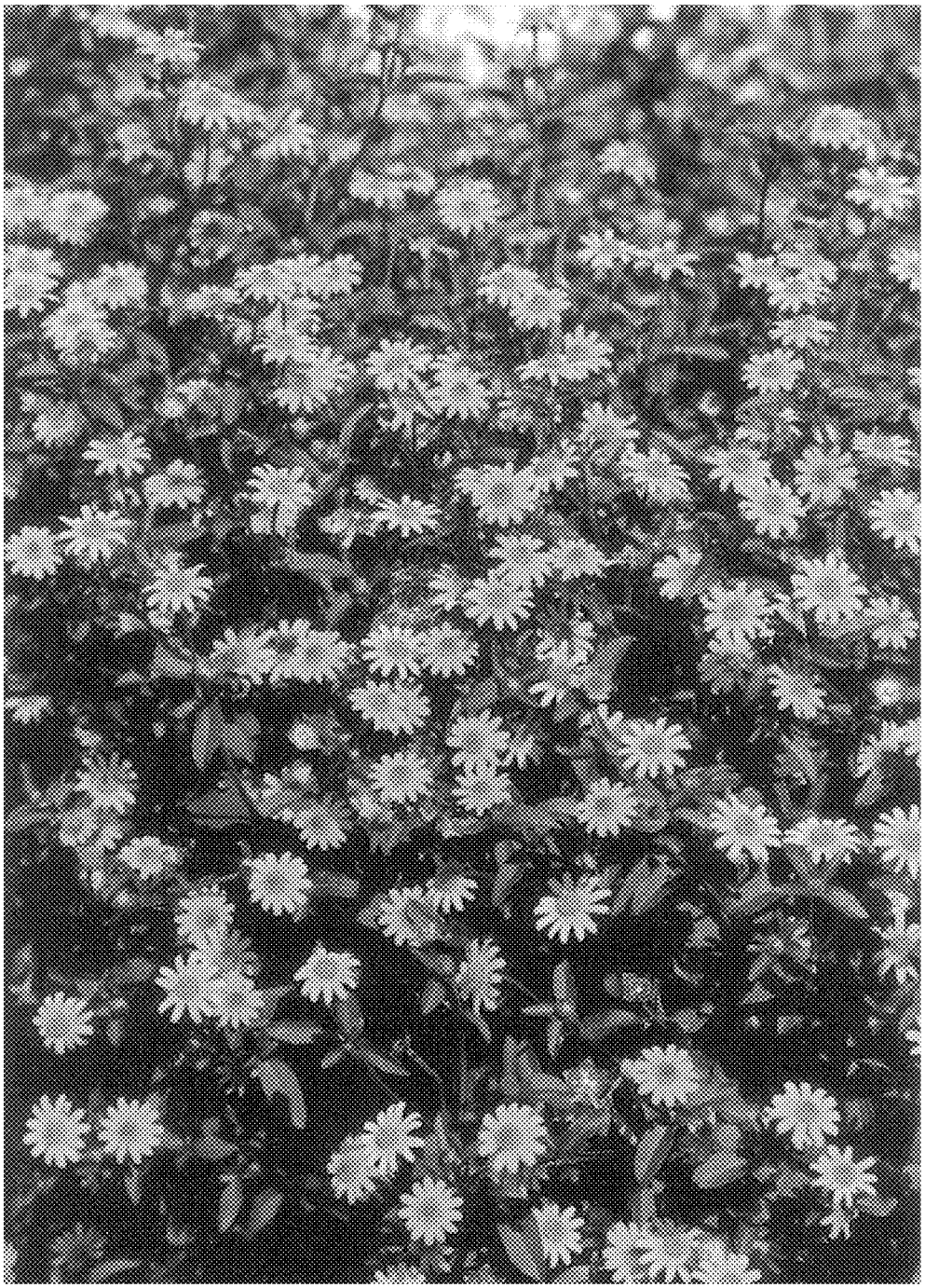

UNITED STATES PATENT AND TRADEMARK OFFICE

CERTIFICATE OF CORRECTION

PATENT NO. : PP 12,297 P2
DATED : December 18, 2001
INVENTOR(S) : Anna M.W.P. Houbraken It is certified that error appears in the above-identified patent and that said Letters Patent is hereby corrected as shown below:

Title page, Item [54] and Column 1, line 1,
Title should read -- SANVITALIA NAMED 'SANTIS 99-3' --

Signed and Sealed this

Eighth Day of October, 2002

*Attest:*

*Attesting Officer*

JAMES E. ROGAN
*Director of the United States Patent and Trademark Office*